(12) United States Patent
Hsueh Liu et al.

(10) Patent No.: US 11,109,476 B2
(45) Date of Patent: Aug. 31, 2021

(54) FILTER

(71) Applicant: HERON NEUTRON MEDICAL CORP., Hsinchu (TW)

(72) Inventors: Yen-Wan Hsueh Liu, Hsinchu (TW); Zhen-Fan You, Luodong Township (TW); Sheng Yang, Hsinchu (TW); Jyi-Tyan Yeh, Zhudong Township (TW)

(73) Assignee: HERON NEUTRON MEDICAL CORP., Hsinchu (TW)

(*) Notice: Subject to any disclaimer, the term of this patent is extended or adjusted under 35 U.S.C. 154(b) by 0 days.

(21) Appl. No.: 16/996,379

(22) Filed: Aug. 18, 2020

(65) Prior Publication Data

US 2020/0383198 A1    Dec. 3, 2020

Related U.S. Application Data

(62) Division of application No. 15/672,672, filed on Aug. 9, 2017, now Pat. No. 10,791,618.

(30) Foreign Application Priority Data

Dec. 2, 2016  (TW) .................................. 105139840

(51) Int. Cl.
*H05H 3/06* (2006.01)
*H05H 7/00* (2006.01)
*A61N 5/10* (2006.01)

(52) U.S. Cl.
CPC ............ *H05H 3/06* (2013.01); *A61N 5/1077* (2013.01); *H05H 7/001* (2013.01);
(Continued)

(58) Field of Classification Search
CPC .. A61N 2005/109; A61N 5/10; A61N 5/1077; A61N 5/1042; G21K 5/00;
(Continued)

(56) References Cited

U.S. PATENT DOCUMENTS 3,255,369 A * 6/1966 Bernard ................ H01F 29/146
                                                          315/501
3,375,452 A * 3/1968 Forsyth ................. G21K 1/093
                                                          315/503
(Continued)

FOREIGN PATENT DOCUMENTS

CN     101529530 A     9/2009
CN     102145206 A     8/2011
(Continued)

OTHER PUBLICATIONS https://en.wikipedia.org/wiki/Lithium_fluoride (Year: 2020).*
(Continued)

*Primary Examiner* — Wyatt A Stoffa
(74) *Attorney, Agent, or Firm* — Birch, Stewart, Kolasch & Birch, LLP

(57) ABSTRACT

A filter is provided. The filter includes a mixed layer. The mixed layer includes aluminum, magnesium fluoride, and lithium fluoride. The mixed layer is composed of 1 part by volume of magnesium fluoride, 0.25 to 1 parts by volume of aluminum, and 0.003 to 0.02 parts by volume of lithium fluoride.

3 Claims, 9 Drawing Sheets

(52) U.S. Cl.
CPC ............... *A61N 2005/109* (2013.01); *A61N 2005/1095* (2013.01); *H05H 2007/004* (2013.01)

(58) Field of Classification Search
CPC ............ G21K 5/04; H05H 3/06; H05H 7/001; H05H 2007/004
See application file for complete search history.

(56) References Cited

U.S. PATENT DOCUMENTS

| | | | | |
|---|---|---|---|---|
| 3,386,040 | A * | 5/1968 | Maschke | H05H 7/06 315/503 |
| 3,778,627 | A * | 12/1973 | Carpenter | H05H 3/06 376/192 |
| 4,090,086 | A * | 5/1978 | Cranberg | H05H 3/06 250/282 |
| 4,139,777 | A * | 2/1979 | Rautenbach | H05H 13/08 376/112 |
| 4,192,998 | A * | 3/1980 | Azam | A61N 5/10 250/515.1 |
| 4,666,651 | A * | 5/1987 | Barjon | A61N 5/10 376/108 |
| 4,996,017 | A * | 2/1991 | Ethridge | H05H 3/06 376/116 |
| 5,073,913 | A * | 12/1991 | Martin | A61N 5/1077 378/34 |
| 5,547,454 | A * | 8/1996 | Horn | A61N 5/1001 600/1 |
| 5,730,918 | A | 3/1998 | Nikolskaja et al. | |
| 6,922,455 | B2 * | 7/2005 | Jurczyk | G21K 5/04 376/144 |
| 8,648,315 | B1 * | 2/2014 | Hailey | H01J 37/08 250/396 R |
| 9,789,340 | B2 * | 10/2017 | Liu | A61N 5/1077 |
| 9,881,711 | B2 * | 1/2018 | Odawara | G21K 5/04 |
| 2010/0195781 | A1 * | 8/2010 | Paul | H05H 6/00 376/185 |
| 2013/0066135 | A1 * | 3/2013 | Rosa | A61N 5/10 600/1 |
| 2014/0094641 | A1 * | 4/2014 | Gall | H05H 7/10 600/1 |
| 2015/0105604 | A1 * | 4/2015 | Liu | G21G 4/02 600/1 |
| 2016/0059040 | A1 * | 3/2016 | Paliwal | A61N 5/1067 378/65 |
| 2016/0351282 | A1 * | 12/2016 | Kumada | C04B 35/6455 |
| 2017/0040075 | A1 * | 2/2017 | Tang | G21G 4/02 |
| 2017/0062086 | A1 * | 3/2017 | Park, Jr. | H05H 3/06 |
| 2017/0178859 | A1 * | 6/2017 | Ryding | C30B 29/20 |
| 2017/0368373 | A1 * | 12/2017 | Sahadevan | A61N 5/1067 |
| 2018/0141869 | A1 * | 5/2018 | Furuya | A61N 5/10 |
| 2018/0214715 | A1 * | 8/2018 | Takayama | A61N 5/1042 |
| 2018/0233246 | A1 * | 8/2018 | Liu | H05H 3/06 |
| 2018/0247784 | A1 * | 8/2018 | Akinwande | H01J 27/26 |
| 2019/0022421 | A1 * | 1/2019 | Liu | G21K 1/10 |
| 2019/0030369 | A1 * | 1/2019 | Mukawa | A61N 5/1064 |
| 2019/0054319 | A1 * | 2/2019 | Wang | A61K 41/0095 |
| 2019/0105512 | A1 * | 4/2019 | Liu | A61N 5/1081 |
| 2019/0105513 | A1 * | 4/2019 | Liu | A61N 5/1081 |
| 2019/0160307 | A1 * | 5/2019 | Liu | G21K 5/04 |
| 2019/0209687 | A1 * | 7/2019 | Yamaguchi | A61N 5/1049 |

FOREIGN PATENT DOCUMENTS

| | | |
|---|---|---|
| CN | 103052425 A | 4/2013 |
| CN | 103180912 A | 6/2013 |
| CN | 104575653 A | 4/2015 |
| CN | 204798657 U | 11/2015 |
| CN | 105120952 A | 12/2015 |
| CN | 205073543 U | 3/2016 |
| DE | 4304667 A1 | 9/1994 |
| EP | 1 895 819 A1 | 3/2008 |
| JP | 2006-47115 A | 2/2006 |
| JP | 2007-242422 A | 9/2007 |
| JP | 2009-189643 A | 8/2009 |
| JP | 2013-19692 A | 1/2013 |
| JP | 2014-115122 A | 6/2014 |
| TW | 201034530 A | 9/2010 |
| TW | 201609217 A | 3/2016 |
| TW | I532056 B | 5/2016 |
| TW | 201634075 A | 10/2016 |
| WO | WO 2016/179381 A1 | 11/2016 |

OTHER PUBLICATIONS https://en.wikipedia.org/wiki/Aluminium (Year: 2020).*
https://en.wikipedia.org/wiki/Magnesium_fluoride (Year: 2020).*
Agosteo et al., "Characterisation of an accelerator-based neutron source for BNCT versus beam energy", Elsevier, Nuclear Instruments and Methods in Physics Research A, 476, (2002), pp. 106-112.
Aleynik of al., "Current progress and future prospects of the VITA based neutron source", Elsevier, Applied Radiation and Isotopes, 88, (2014), pp. 177-179.
Ceballos et al., "Towards the final BSA modeling for the accelerator-driven BNCT facility at INFN LNL", Elsevier, Applied Radiation and Isotopes, 69, (2011), pp. 1660-1663.
Chinese Office Action and Search Report, dated Jun. 25, 2019 for Chinese Application No. 201611247366.4.
Culbertson el al., "In-phantom characterisation studies at the Birmingham Accelarator-Generated epIthermal Neutron Source (BAGINS) BNCT facility", Elsevier, Applied Radiation and Isotopes, 61, (2004), pp. 733-738.
Ghal-Eh et al., "A plastic scintillator-based 2D thermal neutron mapping system for use in BNCT studies", Elsevier, Applied Radiation and Isotopes, 112, (2016), pp. 31-37.
Japanese Office Action, dated Dec. 3, 2018, for Japanese Application No. 2017-165336, with an English machine translation.
Kim et al., "Optimized therapeutic neutron beam for accelerator-based BNCT by analyzing the neutron angular distribution from 7Li(p,n)7Be reaction", Elsevier, Applied Radiation and Isotopes, 67, (2009), pp. 1173-1179.
Minsky et al., "Near threshold 7Li(p,n) 7Be reaction as neutron source for BNCT", Elsevier, Applied Radiation and Isotopes, 106, (2015), pp. 68-71.
Montagnini et al., "Spectrum shaping of accelerator-based neutron beams for BNCT", Elsevier, Nuclear Instruments and Methods in Physics Research A, 476, (2002), pp. 90-98.
Office Action was dated Jul. 19, 2017 for the corresponding application No. 105139840 in Taiwan.
Office Action was dated Mar. 15, 2017 for the corresponding application No. 105139840 in Taiwan.

* cited by examiner

FILTER

CROSS REFERENCE TO RELATED APPLICATIONS

The present application is based on, and claims priority from, Taiwan Application Serial Number 105139840, filed on Dec. 2, 2016, the disclosure of which is hereby incorporated by reference herein in its entirety. This application is a Divisional application of U.S. patent application Ser. No. 15/672,672, filed on Aug. 9, 2017, the entire of which is incorporated by reference herein.

TECHNICAL FIELD

The technical field relates to a neutron beam source generator and a filter thereof.

BACKGROUND

In the principle of the boron neutron capture therapy (BNCT), a boron-containing drug is preferentially accumulated in tumor cells through the blood circulation, and the tumor tissue is irradiated by a neutron beam. As such, the boron absorbs neutron to produce high LET alpha particle and $^7Li$ ion, which may locally destroy the tumor cells without damaging the normal tissues.

BNCT only causes extremely small damage to the patient, and the surgical operation and anesthetic can be omitted. If thermal neutrons are used in BNCT for a brain tumor, the skull of the patient needs to be opened up. If epithermal neutrons are used in BNCT for the brain tumor, the step of opening the skull can be omitted.

Most of the neutron beam sources in BNCT are from research reactors. In general, research reactors cannot be located in hospitals, and therefore the doctors and patients must move to the location of research reactors. On the other hand, accelerator-based neutron beam sources can be built in hospitals. It not only costs less, but also saves time for the doctors and the patients.

Accordingly, an accelerator-based neutron beam source for BNCT is called for.

SUMMARY

One embodiment of the disclosure provides a neutron beam source generator. The neutron beam source generator includes an accelerator connecting to a beryllium target through a channel, a filter and a collimator. The beryllium target is disposed at an end of the channel and adjacent to the filter. The filter is disposed between the beryllium target and the collimator. The channel and the beryllium target have an angle α therebetween, and the angle α is between 0° and 90°, wherein the channel and a direction normal to a surface of the filter have an angle β therebetween, and the angle β is between 0° and 90°. The cross-section of the channel has a non-circular shape.

One embodiment of the disclosure provides a filter. The filter includes a mixed layer of aluminum, magnesium fluoride, and lithium fluoride. The mixed layer is composed of 1 part by volume of magnesium fluoride, 0.25 to 1 parts by volume of aluminum, and 0.003 to 0.02 parts by volume of lithium fluoride.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein.

DETAILED DESCRIPTION

Figure 1:
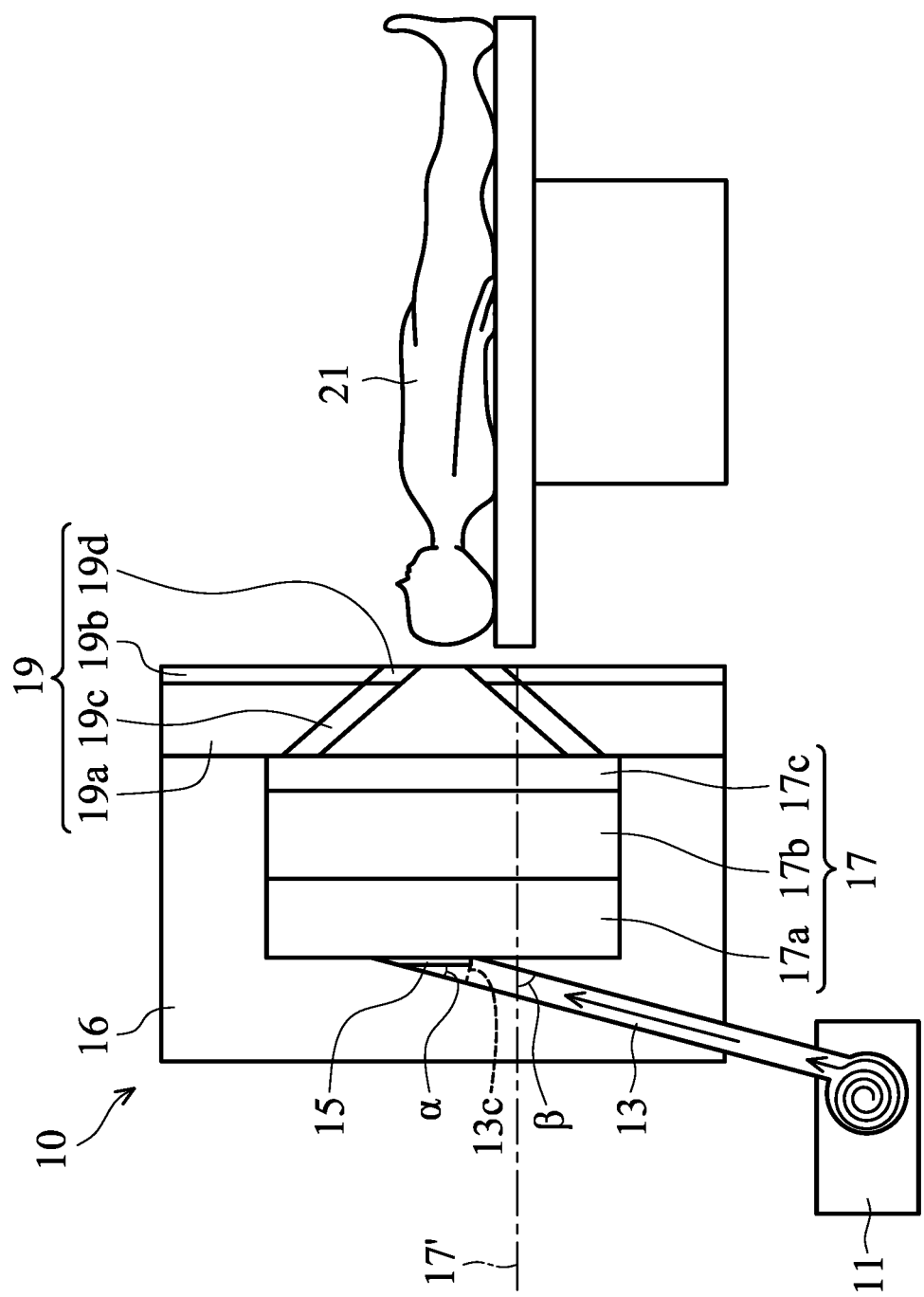
FIGS. 1 and 2 show neutron beam sources in embodiments of the disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

As shown in FIG. 1, a neutron beam source generator 10 in one embodiment of the disclosure is constructed from following principal parts: an accelerator 11, a target 15, a channel 13 connecting the accelerator 11 and the target 15, a filter 17, and a collimator 19. The target 15 is located at an end of the channel 13 and adjacent to the filter 17. For example, the accelerator 11 can be a cyclotron commercially available from Advanced Cyclotron Systems Inc. The accelerator 11 is used to provide a proton beam with energy of 19 MeV to 30 MeV to collide with the target 15, thereby producing fast neutrons.

The fast neutrons passing through the filter 17 and a collimator element 19 turn into an epithermal neutron beam. The International Atomic Energy Agency (IAEA) suggests that a desirable minimum epithermal neutron beam intensity for BNCT would be $10^9$ epithermal neutrons $cm^{-2} \cdot s^{-1}$, and the fast neutron dose and the gamma ray dose per epithermal neutron fluence would be less than $2.0 \times 10^{-11}$ $cGy \cdot cm^2/n$, respectively. Since the criterion for gamma ray dose component is easily achieved, the disclosure mainly discusses the epithermal neutron flux and the fast neutron dose component. An overly low epithermal neutron flux may prolong the irradiation time of the therapy for a patient 21. An overly high fast neutron flux may damage the normal tissues of the patient 21. The protons (produced by the accelerator 11) with overly high energy will increase the difficulty of shielding design without further increasing the neutron yield. The protons (produced by the accelerator 11) with overly low energy may produce neutrons of insufficient yield, and the current of the protons would need to be increased to compensate for the neutron yield.

In one embodiment, the target 15 is composed of beryllium.

As shown in FIG. 1, the channel 13 and the target 15 have an angle α therebetween, and the channel 13 and a direction 17' normal to the surface of the filter 17 have an angle β therebetween. In one embodiment, the larger angle β is, the more obvious the oblique incident effect of the protons (passing through the channel 13 and colliding the target 15 through an incident angle) is. For example, when the angle β is changed from 0° to 45°, the fast neutron dose component of the neutron beam at the beam exit is reduced by 25%. When the angle β is changed from 45° to 90°, the fast neutron dose component can be reduced by 57%.

A general cross-section of a channel and a general target have circular shapes. In the design of the oblique incident proton beam to the target, if a cross-section of the channel has a circular shape, the cross-section of the channel will project onto the target to define a projection with an oval or elliptical shape. On the other hand, if a cross-section of the channel has an oval or elliptical shape, the cross-section of the channel will project onto the target to define a projection with a circular, an elliptical, or an oval shape. In the case of the target area being fixed (under equal heat dissipation effect), smaller oval or elliptical cross-section of the channel reduces the neutron leakage. As such, the cross-section of the channel has a non-circular shape in one embodiment.

Figure 8A:
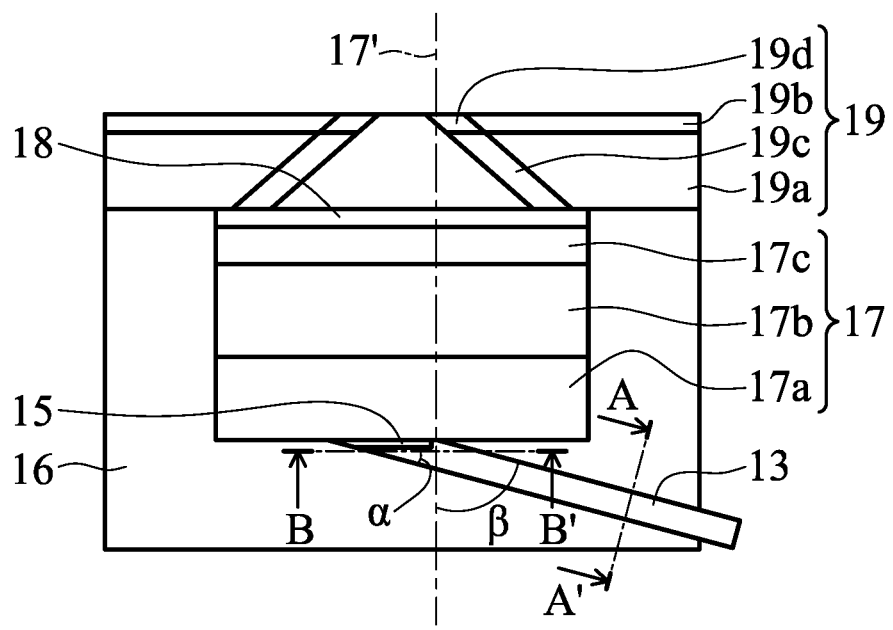
Figure 8B:
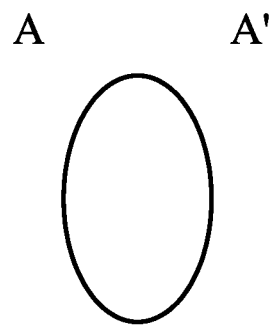
FIGS. 8B and 8D show various cross-sectional views of FIG. 8A along line A-A' in embodiments of the disclosure.
Figure 8C:
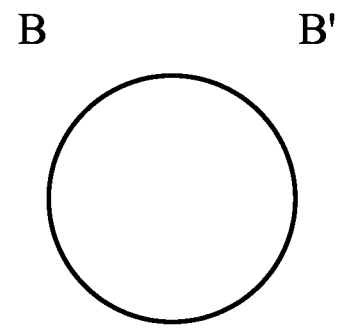
FIGS. 8C and 8E show various cross-sectional views of FIG. 8A along line B-B' in embodiments of the disclosure.
Figure 8D:
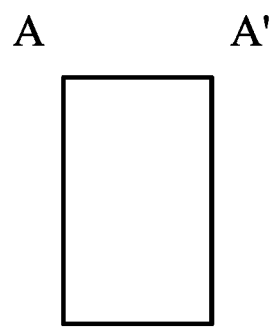
Figure 8E:
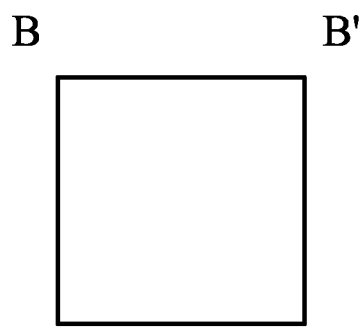

In one embodiment, the angle between the target and the channel is changed to adjust the shape of the cross-section 13c of the channel, such that the cross-section 13c projects onto the target to define a projection, and the projection has an area greater than or equal to that of the cross-section 13c. In particular, the cross-section 13c projects onto the target to define the projection with an area larger than or equal to that of the cross-section 13c of the channel. FIGS. 8B and 8D illustrate various cross-sectional views of FIG. 8A along line A-A' according to some embodiments of the present disclosure. FIGS. 8C and 8E illustrate various cross-sectional views of FIG. 8A along line B-B' according to some embodiments of the present disclosure. For example, when the cross-section of the channel has an oval or elliptical shape (for example, FIG. 8B), the cross-section of the channel projects onto the target to define a projection with a circle, an elliptical (for example, FIG. 8C), or an oval shape. When the cross-section of the channel has a rectangular shape (for example, FIG. 8D), the cross-section of the channel projects onto the target to define a projection with a square (for example, FIG. 8E) or rectangular shape. In one embodiment, the cross-section of the channel projects onto the target to define a projection overlapping the target.

In one embodiment, the oval or elliptical cross-section 13c of the channel is vertical to the wall of the channel 13. The cross-section 13c of the channel 13 has a lateral size (e.g. minor axis of the oval/elliptical shape) is equal to the lateral size of the target×sin α. The cross-section 13c of the channel 13 has a longitudinal size (e.g. major axis of the oval/elliptical shape) is equal to the longitudinal size of the target 15. Therefore, the cross-section 13c of the channel 13 projects onto the target to define a projection substantially overlapping the target 15. For example, the cross-section 13c of the channel 13 projects onto the target 15 to define a projection (a circle with a diameter of d), the cross-section 13c of the channel 13 has an oval or elliptical shape with a major axis of d and a minor axis of d×sin α. When the cross-section 13c of the channel 13 projects onto the target 15 to define a projection (a square with a side length of d), the cross-section 13c of the channel 13 has a rectangular shape with a long side length of d and a short side length of d×sin α. Except the above shapes, one skilled in the art may select the appropriate shape of the projection defined by the cross-section 13c of the channel 13 projecting onto the target 15, and the corresponding cross-section 13c. The angle α between the target 15 and the cross-section 13c of the channel 13 can be changed to adjust the shape of the cross-section 13c of the channel 13 for enhancing the epithermal neutron flux.

In FIG. 1, the target 15 adjoins the filter 17. Alternatively, the channel 13 and the direction 17' normal to the surface of the filter 17 have an angle β (45° to 90°) therebetween, and the channel 13 and the target 15 have an angle α therebetween. The range of the angle α is the same as previously stated, and its related description is therefore omitted here.

The filter 17 can be a tri-layered structure as shown in FIG. 1, but it can include a single-layered structure or another multi-layered structure (more than three layers). In one embodiment, the filter 17 has a total thickness of 54 cm to 67.5 cm. An overly thin filter 17 cannot efficiently reduce the fast neutron dose component. An overly thick filter cannot produce sufficient epithermal neutron flux of the neutron beam.

In some embodiment, the filter 17 includes a single layer of aluminum, magnesium fluoride, and lithium fluoride mixed layer, wherein the mixed layer is composed of 1 part by volume of magnesium fluoride, 0.25 to 1 parts by volume of aluminum, and 0.003 to 0.02 parts by volume of lithium fluoride.

In one embodiment, the filter 17 is a tri-layered structure, in which a second layer 17b is disposed between a first layer 17a and a third layer 17c, and the first layer 17a is disposed between the target 15 and the second layer 17b, such that the neutrons (produced by collision of the protons with the target 15) sequentially pass through the first layer 17a, the second layer 17b, and the third layer 17c. The first layer 17a is composed of iron, and the neutrons with energy higher than 1 MeV will be moderated to energy less than 1 MeV by inelastic scattering with iron. In one embodiment, the first layer 17a has a thickness of 15 cm to 26 cm. A first layer 17a with an overly thin thickness will cause too many neutrons having energy higher than 1 MeV. A first layer 17a with an overly thick thickness will reduce thicknesses of other layers for shaping the neutrons with energy less than 1 MeV, thereby affecting the neutron beam quality. The second layer 17b is composed of 1 part by volume of aluminum fluoride, 0.25 to 1 parts by volume of aluminum, and 0.013 to 0.02 parts by volume of lithium fluoride. In one embodiment, the second layer 17b has a thickness of 20 cm to 35 cm. When the total thickness of the filter 17 is fixed, a second layer 17b with an overly thick thickness will result in an overly thin third layer 17c, thereby fail to sufficiently moderate the neutrons and results in an overly high fast neutron dose rate. A second layer 17b with an overly thin thickness will cause an overly thick third layer. The fast neutron dose rate of the neutron beam can be sufficiently reduced. However, the epithermal neutron flux will be overly low. The third layer 17c is composed of 1 part by weight of lithium fluoride and 99 to 100 parts by weight of magnesium fluoride, wherein the lithium fluoride is dispersed in the magnesium fluoride. In one embodiment, the third layer 17c of the tri-layered filter 17 can be a mixed layer of aluminum, magnesium fluoride, and lithium fluoride, wherein the mixture layer is composed of 1 part by volume of magnesium fluoride, 0.25 to 1 parts by volume of aluminum, and 0.003 to 0.02 parts by volume of lithium fluoride. In one case, the aluminum and the lithium fluoride are dispersed in the magnesium fluoride.

In one embodiment, the third layer 17c has a thickness of 5 cm to 10 cm. A third layer 17c with an overly thick thickness will overly moderate the neutrons, thereby producing a neutron beam with an overly low epithermal neutron flux. A third layer 17c with an overly thin thickness will be insufficient to moderate the neutrons, thereby producing a neutron beam with an overly high fast neutron dose rate. In one embodiment, the sidewall of the first layer 17a, such as at the external peripheral of the first layer 17a was surrounded by the same material as the second layer 17b. In one embodiment, the area of the first layer 17a is smaller than the area of the second layer 17b, and the area of the second layer 17b is smaller than the area of the third layer 17c (mixture layer). In one embodiment, the filter is applied in a neutron beam source generator.

In one embodiment, a reflector 16 (e.g. lead wall with a thickness of 15 cm) can be disposed outside the filter 17 to increase the final epithermal neutron flux.

Figure 2:
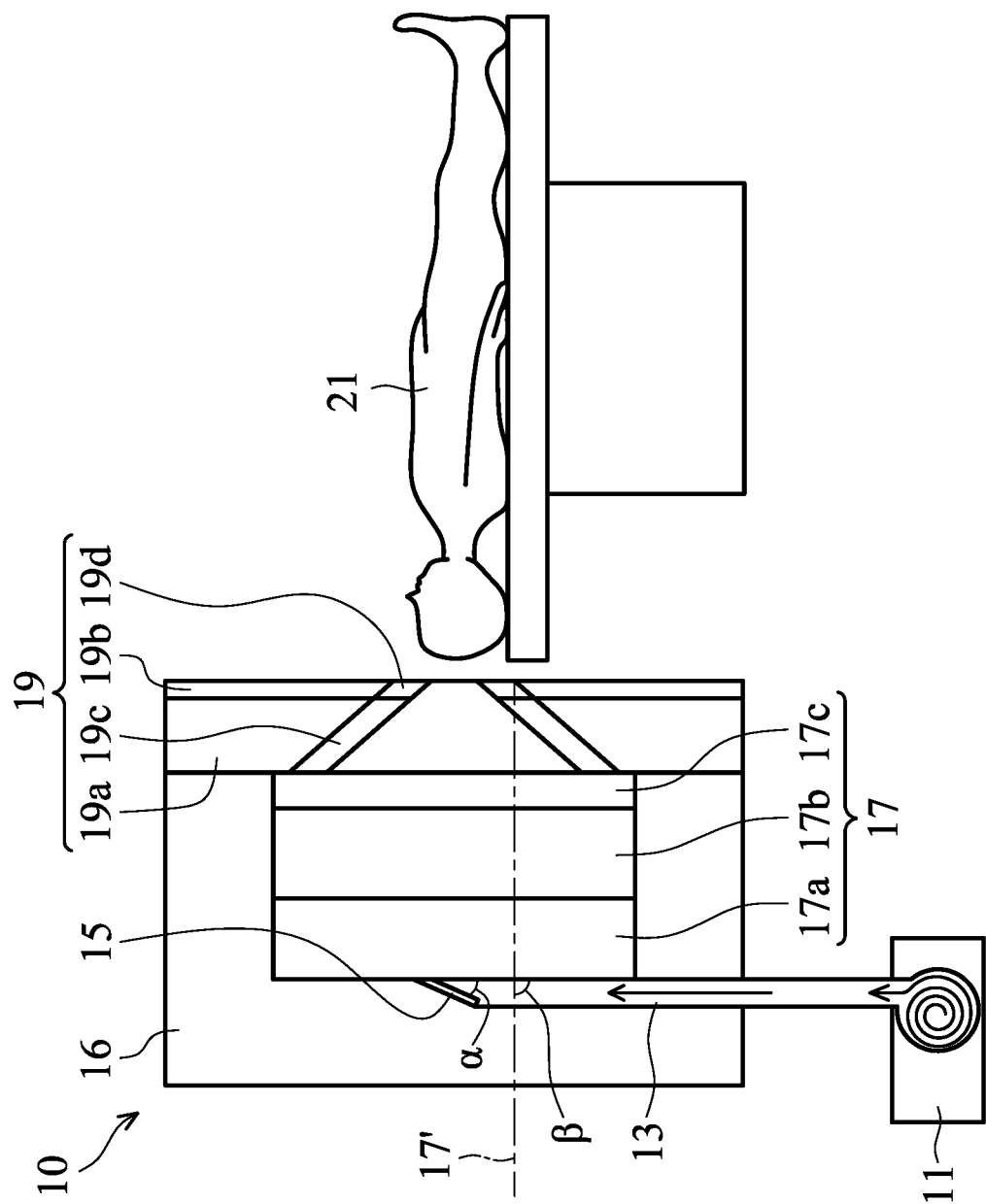

As shown in FIGS. 1 and 2, a collimator element 19 can be disposed between the third layer 17c and the patient 21. In other words, the filter 17 is disposed between the target 15 and the collimator element 19. The design of the collimator element 19 can be referred in Y-W H. Liu, T. T. Huang, S. H. Jiang, H. M. Liu, (2004) "Renovation of Epithermal Neutron Beam for BNCT at THOR," Appl. Radiat. Isot. 61, 1039-1043. The collimator element 19 may focus and maintain the epithermal neutron flux intensity, and simultaneously reduce the fast neutron dose rate. In the design of FIG. 1, most of the neutron beams (produced by the protons colliding and passing through the target 15) directly enter the filter. In the design of FIG. 2, most of the neutron beams (produced by the protons colliding and passing through the target 15) are reflected by the reflector 16 (such as the lead wall at the back side of the target 15) to enter the filter 17. In some embodiment, the thickness of the reflector 16 at the backside of the target 15 is increased to 45 cm to increase the reflected neutron flux. In FIGS. 1 and 2, the first layer 17a, the second layer 17b, and the third layer 17c of the filter 17 have a same area. Alternatively, the third layer 17c has the largest area, the second layer 17b has an area of 81% to 100% of the area of the third layer 17c, and the first layer 17a has an area of 16% to 100% of the area of the third layer 17c, thereby completing a narrow front and wide back filter. In one embodiment, the material of second filter 17b may further be used to surround the first layer 17a. Compared to the column-shaped filter, the narrow front and wide back filter may enhance the epithermal neutron flux.

As shown in FIGS. 1 and 2, the collimator element 19 includes a collimator material 19c and shielding materials 19a, 19b, and 19d. The stacked shielding materials 19a and 19b include openings, and the collimator material 19c and the shielding layer 19d are respectively disposed on sidewalls of the openings of the shielding materials 19a and 19b. In one embodiment, the shielding material 19a is polyethylene mixed with 40 wt % of lithium carbonate, the shielding material 19b is Teflon, the collimator material 19c is bismuth, and the shielding material 19d is polyethylene mixed with 40 wt % of lithium carbonate, wherein lithium in the lithium carbonate is enriched $^6$Li. In some embodiment, the thickness of shielding material 19a (e.g. polyethylene mixed with 40 wt % of lithium carbonate) is reduced from 20 cm to 5 cm, and the original 15 cm of the shielding material 19a is replaced with lead, thereby increasing the epithermal neutron flux. In addition, because the above design may increase the epithermal neutron flux, and the proton beam produced by the accelerator may have a lower energy (e.g. less than 30 MeV). For example, the accelerator 11 producing protons with energy of 19 MeV to 24 MeV can be applied to the above design, thereby reducing the cost of the accelerator 11.

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

EXAMPLES

In the experiments described below, the simulation calculation software used was MCNPX, developed by Los Alamos National Laboratory, and the cross-section library was ENDF/B-7.

In Comparative Example 1 and Examples 1 to 4, the simulation condition was accelerator producing protons with energy of 30 MeV and current of 1 mA (30 MeV/1 mA), and the target being beryllium with a circular shape (diameter of 19 cm) and a thickness of 0.55 cm. The first layer of the filter is composed of iron. The second layer of the filter was composed of 1 part by volume of aluminum fluoride, 0.517 parts by volume of aluminum, and 0.017 parts by volume of lithium fluoride. The third layer of the filter was composed of 1 part by weight of lithium fluoride and 99 parts by weight of magnesium fluoride. The first layer had a thickness of 27.5 cm, the second layer had a thickness of 32.5 cm, and the third layer had a thickness of 7.5 cm. The filter constructed by the first layer, the second layer, and the third layer was a column-shaped filter with a radius of 50 cm. The filter was integrated with the collimator element 19 as disclosed in in Y-W H. Liu, T. T. Huang, S. H. Jiang, H. M. Liu, (2004) "Renovation of Epithermal Neutron Beam for BNCT at THOR," Appl. Radiat. Isot. 61, 1039-1043. A bismuth layer 18 with a thickness 5 cm was disposed between the tri-layered filter 17 and the collimator element 19.

Comparative Example 1

Figure 3:
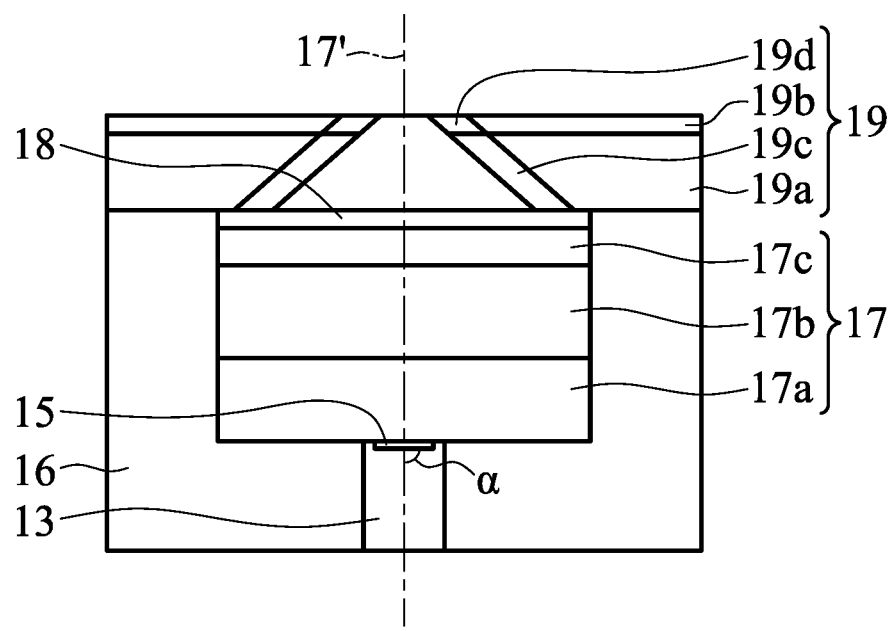
FIGS. 3-7, 8A, and 9-13 show relative locations between a channel, a target, a filter, and a collimator in embodiments of the disclosure.

As shown in FIG. 3, the target 15 adjoined the filter 17, and the channel 13 is vertical to the target 15. The angle α between the channel 13 and the target 15 was 90°, and the angle β between the channel 13 and the direction 17' (normal to the surface of the filter 17) was 0°. In other words, the channel 13 and the direction 17' were toward to the same orientation. The cross-section 13c of the channel 13 has a circular shape with a diameter of 20 cm. The epithermal neutron flux, the fast neutron dose rate, and the fast neutron dose per epithermal neutron fluence of the neutron beam produced by the neutron beam source generator are tabulated in Table 1.

Example 1

Figure 4:
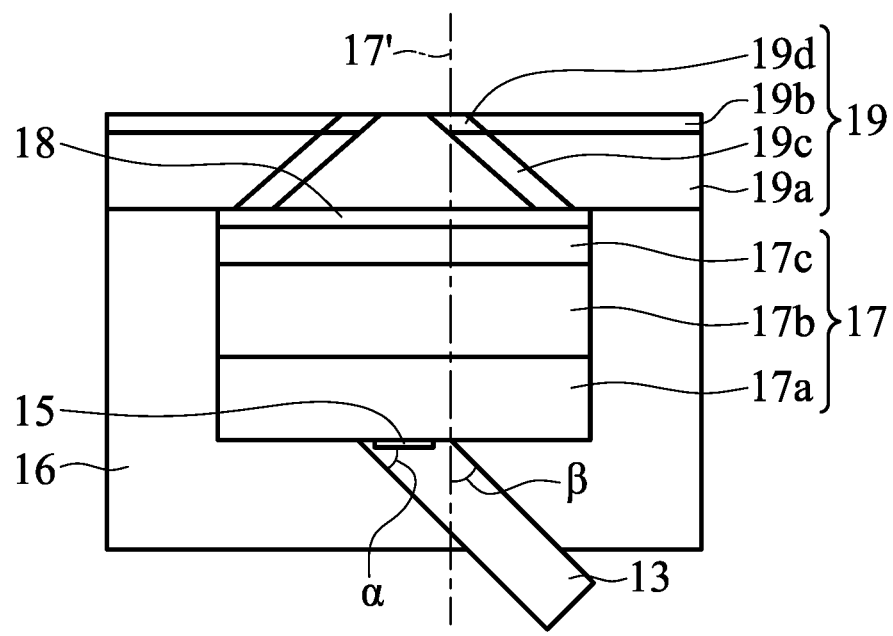

As shown in FIG. 4, the target 15 adjoined the filter 17, the angle α between the channel 13 and the target 15 was 45°, and the angle β between the channel 13 and the direction 17' (normal to the surface of the filter 17) was 45°. The cross-section 13c of the channel 13 has a circular shape with a diameter of 20 cm. The epithermal neutron flux, the fast neutron dose rate, and the fast neutron dose per epithermal neutron fluence of the neutron beam produced by the neutron beam source generator are tabulated in Table 1.

Example 2

Figure 5:
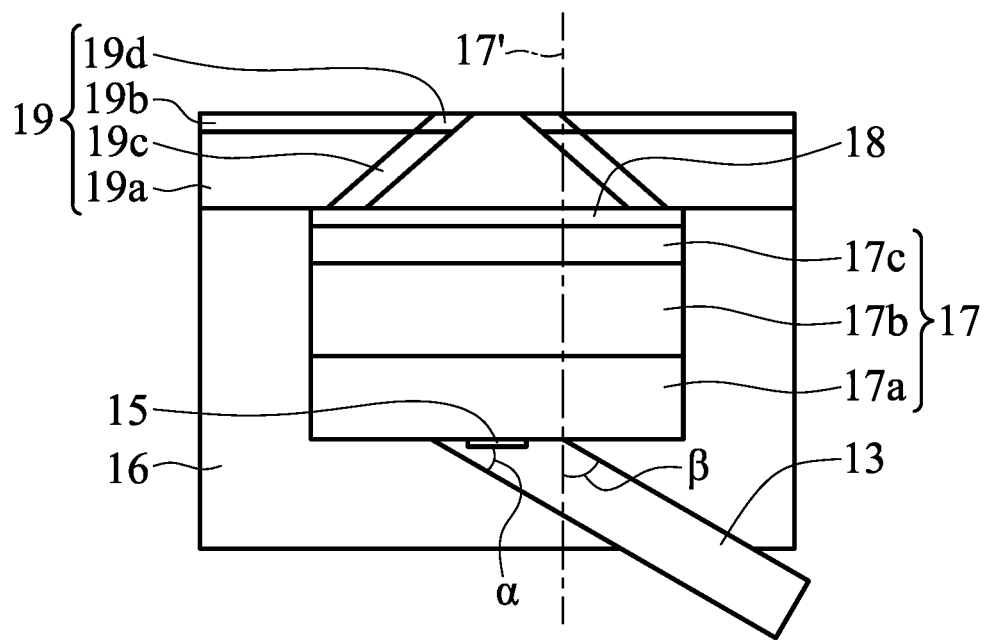

As shown in FIG. 5, the target 15 adjoined the filter 17, the angle α between the channel 13 and the target 15 was 30°, and the angle β between the channel 13 and the direction 17' (normal to the surface of the filter 17) was 60°. The cross-section 13c of the channel 13 has a circular shape with a diameter of 20 cm. The epithermal neutron flux, the fast neutron dose rate, and the fast neutron dose per epithermal neutron fluence of the neutron beam produced by the neutron beam source generator are tabulated in Table 1.

Example 3

Figure 6:
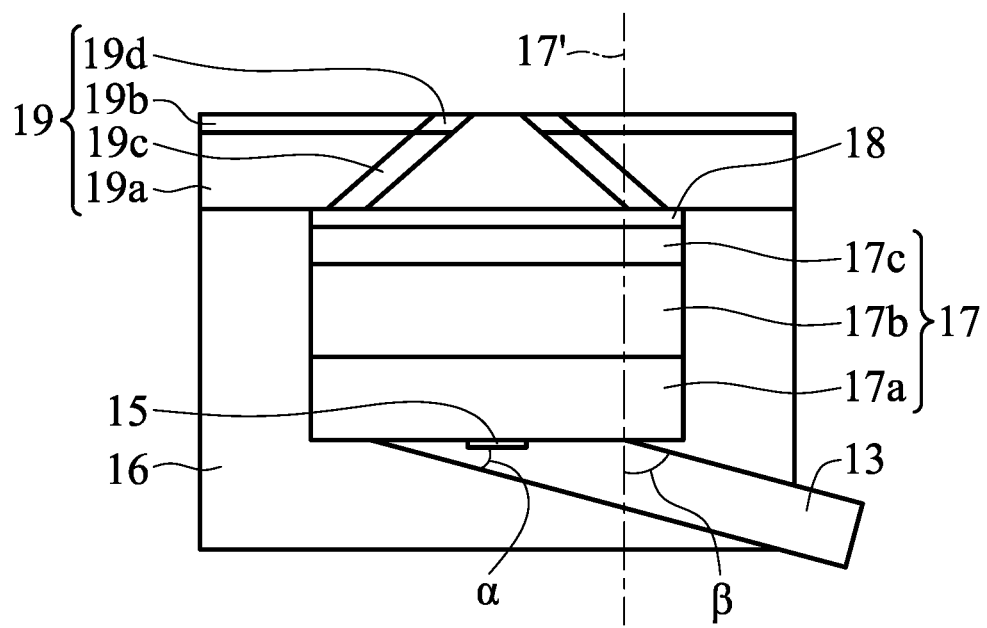

As shown in FIG. 6, the target 15 adjoined the filter 17, the angle α between the channel 13 and the target 15 was 15°, and the angle β between the channel 13 and the direction 17' (normal to the surface of the filter 17) was 75°. The cross-section 13c of the channel 13 has a circular shape with a diameter of 20 cm. The epithermal neutron flux, the fast neutron dose rate, and the fast neutron dose per epithermal neutron fluence of the neutron beam produced by the neutron beam source generator are tabulated in Table 1.

Example 4

Figure 7:
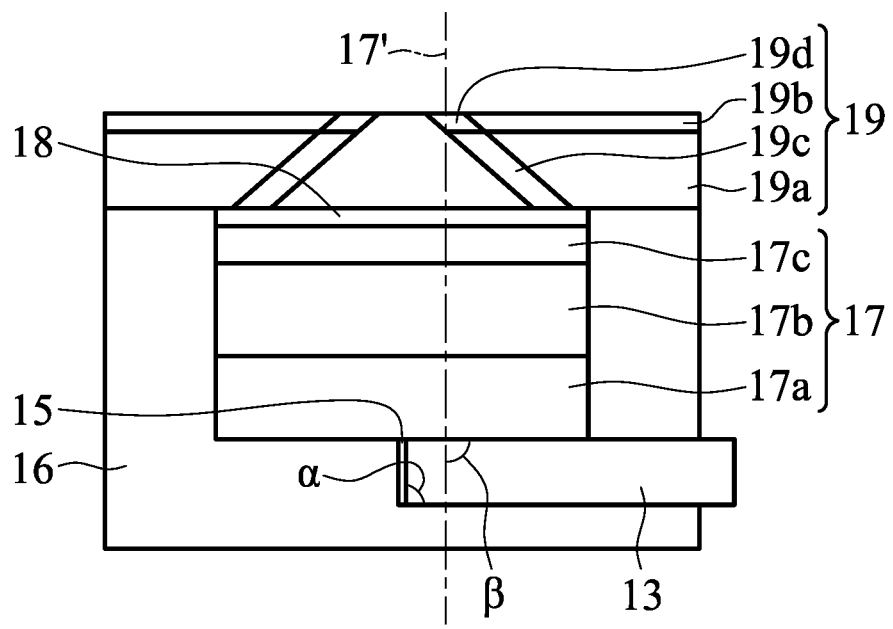

As shown in FIG. 7, the target 15 was vertical to the filter 17, and the channel 13 was vertical to the target 15. The angle α between the channel 13 and the target 15 was 90°, and the angle β between the channel 13 and the direction 17' (normal to the surface of the filter 17) was 90°. The cross-section 13c of the channel 13 has a circular shape with a diameter of 20 cm. The epithermal neutron flux, the fast neutron dose rate, and the fast neutron dose per epithermal neutron fluence of the neutron beam produced by the neutron beam source generator are tabulated in Table 1.

TABLE 1

|  | Comparative Example 1 (FIG. 3) | Example 1 (FIG. 4) | Example 2 (FIG. 5) | Example 3 (FIG. 6) | Example 4 (FIG. 7) |
|---|---|---|---|---|---|
| Angle α between channel and target, angle β between channel and direction normal to the surface of the filter | α = 90°, β = 0° | α = 45°, β = 45° | α = 30°, β = 60° | α = 15°, β = 75° | α = 90°, β = 90° |
| Epithermal neutron flux (n · cm$^{-2}$ · s$^{-1}$) (1 standard deviation) | $2.53 \times 10^9$ (0.13%) | $2.55 \times 10^9$ (0.13%) | $2.51 \times 10^9$ (0.13%) | $2.46 \times 10^9$ (0.14%) | $2.00 \times 10^9$ (0.15%) |
| Fast neutron dose per epithermal neutron fluence (cGy · cm$^2$/n) (1 standard deviation) | $2.68 \times 10^{-11}$ (1.18%) | $1.99 \times 10^{-11}$ (1.20%) | $1.77 \times 10^{-11}$ (1.28%) | $1.55 \times 10^{-11}$ (1.20%) | $1.12 \times 10^{-11}$ (1.32%) |
| Fast neutron dose rate (cGy · s$^{-1}$) (1 standard deviation) | 0.068 (1.17%) | 0.051 (1.19%) | 0.044 (1.27%) | 0.038 (1.19%) | 0.022 (1.31%) |

As shown in Table 1, the angle β between the neutron beam through the channel and the direction normal to the surface of the filter could efficiently reduce the fast neutron dose per epithermal neutron fluence.

Example 5

Example 5 was similar to Example 3 (see FIG. 6) except that the thickness of the first layer 17a was 22 cm, the thickness of the second layer 17b was 25 cm, the thickness of the third layer 17c was 10 cm, and the total thickness of the filter was 57 cm (reduced by 10.5 cm, compared to the total thickness of the filter in Example 3). The epithermal neutron flux, the fast neutron dose rate, and the fast neutron dose per epithermal neutron fluence of the neutron beam produced by the neutron beam source generator are tabulated in Table 2.

Example 6

Example 6 was similar to Example 4 (see FIG. 7) except that the thickness of the first layer 17a was 22 cm, the thickness of the second layer 17b was 25 cm, the thickness of the third layer 17c was 10 cm, and the total thickness of the filter was 57 cm (reduced by 10.5 cm, compared to the total thickness of the filter in Example 4). The epithermal neutron flux, the fast neutron dose rate, and the fast neutron dose per epithermal neutron fluence of the neutron beam produced by the neutron beam source generator are tabulated in Table 2.

As shown in Table 2, a thinner filter could be used in the oblique incident neutron beam source generator, thereby achieving higher epithermal neutron flux.

Example 7

Example 7 was similar to Example 5 except that the cross-section 13c of the channel 13 was replaced from the circular shape with an elliptical shape (major axis=20 cm, minor axis=5.2 cm). As such, the projection of the cross-section of the channel 13 projected onto the target 15 completely overlapped the target 15, as shown in FIG. 8. The epithermal neutron flux, the fast neutron dose rate, and the fast neutron dose per epithermal neutron fluence of the neutron beam produced by the neutron beam source generator are tabulated in Table 3.

Example 8

Figure 9:
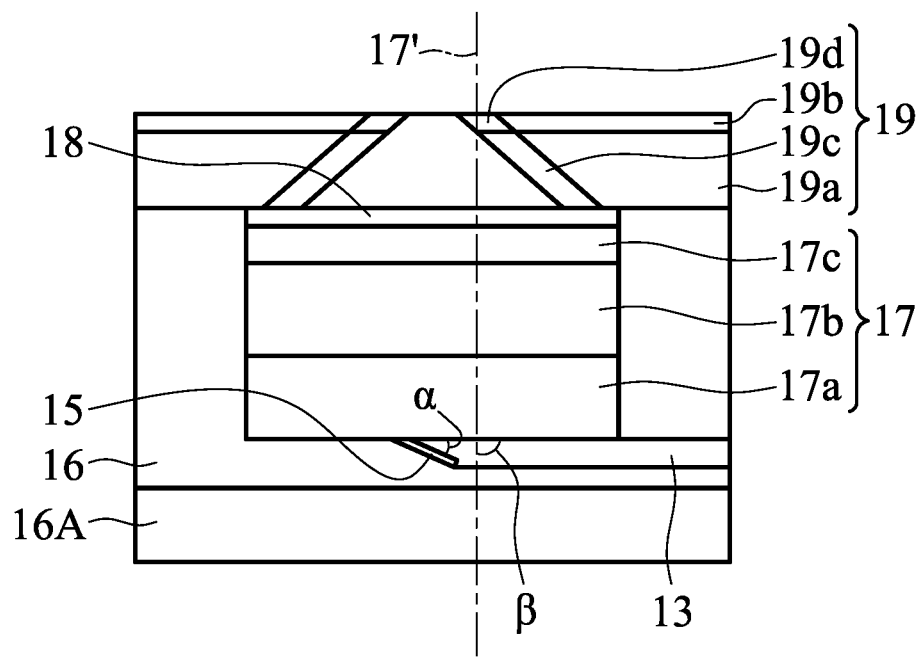

Example 8 was similar to Example 6, and the differences in Example 8 was the target 15 and the filter 17 having an angle of 15° therebetween, as shown in FIG. 9. Moreover, the cross-section 13c of the channel 13 being replaced from the circular shape with an elliptical shape (major axis=20 cm, minor axis=5.2 cm). As such, the projection of the cross-section of the channel 13 projected onto the target 15 completely overlapped the target 15. The epithermal neutron flux, the fast neutron dose rate, and the fast neutron dose per epithermal neutron fluence of the neutron beam produced by the neutron beam source generator are tabulated in Table 3.

TABLE 2

|  | Comparative Example 1 | Example 3 | Example 5 (FIG. 6) | Example 4 | Example 6 (FIG. 7) |
|---|---|---|---|---|---|
| Filter thickness (cm) | 67.5 | 67.5 | 57 | 67.5 | 57 |
| Epithermal neutron flux (n · cm$^{-2}$ · s$^{-1}$) (1 standard deviation) | $2.53 \times 10^9$ (0.13%) | $2.46 \times 10^9$ (0.14%) | $3.55 \times 10^9$ (0.11%) | $2.00 \times 10^9$ (0.15%) | $2.86 \times 10^9$ (0.13%) |
| Fast neutron dose per epithermal neutron fluence (cGy · cm$^2$/n) (1 standard deviation) | $2.68 \times 10^{-11}$ (1.18%) | $1.55 \times 10^{-11}$ (1.20%) | $3.15 \times 10^{-11}$ (0.79%) | $1.12 \times 10^{-11}$ (1.32%) | $2.03 \times 10^{-11}$ (0.92%) |
| Fast neutron dose rate (cGy · s$^{-1}$) (1 standard deviation) | 0.068 (1.17%) | 0.038 (1.19%) | 0.112 (0.78%) | 0.022 (1.31%) | 0.058 (0.91%) |

TABLE 3

|  | Comparative Example 1 | Example 5 (FIG. 6) | Example 7 (FIG. 8) | Example 6 (FIG. 7) | Example 8 (FIG. 9) |
|---|---|---|---|---|---|
| Cross-section shape of Channel | Circular | Circular | Elliptical | Circular, $\alpha = 90°$, $\beta = 90°$ | Elliptical, $\alpha = 15°$, $\beta = 90°$ |
| Filter thickness (cm) | 67.5 | 57 | 57 | 57 | 57 |
| Epithermal neutron flux (n · cm$^{-2}$ · s$^{-1}$) (1 standard deviation) | $2.53 \times 10^9$ (0.13%) | $3.55 \times 10^9$ (0.11%) | $4.10 \times 10^9$ (0.11%) | $2.86 \times 10^9$ (0.13%) | $4.08 \times 10^9$ (0.14%) |
| Fast neutron dose per epithermal neutron fluence (cGy · cm$^2$/n) (1 standard deviation) | $2.68 \times 10^{-11}$ (1.18%) | $3.15 \times 10^{-11}$ (0.79%) | $2.92 \times 10^{-11}$ (0.75%) | $2.03 \times 10^{-11}$ (0.92%) | $2.48 \times 10^{-11}$ (0.98%) |
| Fast neutron dose rate (cGy · s$^{-1}$) (1 standard deviation) | 0.068 (1.17%) | 0.112 (0.78%) | 0.120 (0.74%) | 0.058 (0.91%) | 0.101 (0.97%) |

As shown in Table 3, the smaller elliptical cross-section of the channel could reduce the neutron leakage to further enhance the epithermal neutron flux when the target area was fixed (same thermal dissipation effect), in which the elliptical cross-section was adjusted according to the angle between the cross-section of the channel and the target.

Example 9

Example 9 was similar to Example 8 except that the thickness of the reflector 16A (e.g. lead) at the backside of the target 15 was increased by 15 cm. The epithermal neutron flux, the fast neutron dose rate, and the fast neutron dose per epithermal neutron fluence of the neutron beam produced by the neutron beam source generator are tabulated in Table 4.

TABLE 4

|  | Comparative Example 1 | Example 8 (FIG. 9) | Example 9 (FIG. 9) |
|---|---|---|---|
| Reflector thickness (cm) | 30 | 30 | 45 |
| Filter thickness (cm) | 67.5 | 57 | 57 |
| Epithermal neutron flux (n · cm$^{-2}$ · s$^{-1}$) (1 standard deviation) | $2.53 \times 10^9$ (0.13%) | $4.08 \times 10^9$ (0.14%) | $4.40 \times 10^9$ (0.10%) |
| Fast neutron dose per epithermal neutron fluence (cGy · cm$^2$/n) (1 standard deviation) | $2.68 \times 10^{-11}$ (1.18%) | $2.48 \times 10^{-11}$ (0.98%) | $2.34 \times 10^{-11}$ (0.75%) |
| Fast neutron dose rate (cGy · s$^{-1}$) (1 standard deviation) | 0.068 (1.17%) | 0.101 (0.97%) | 0.103 (0.74%) |

As shown in Table 4, increasing the thickness of the reflector (e.g. reflector 16A) at the backside of the target could increase the epithermal neutron flux yet hardly increase the fast neutron dose rate.

Example 10

Figure 10:
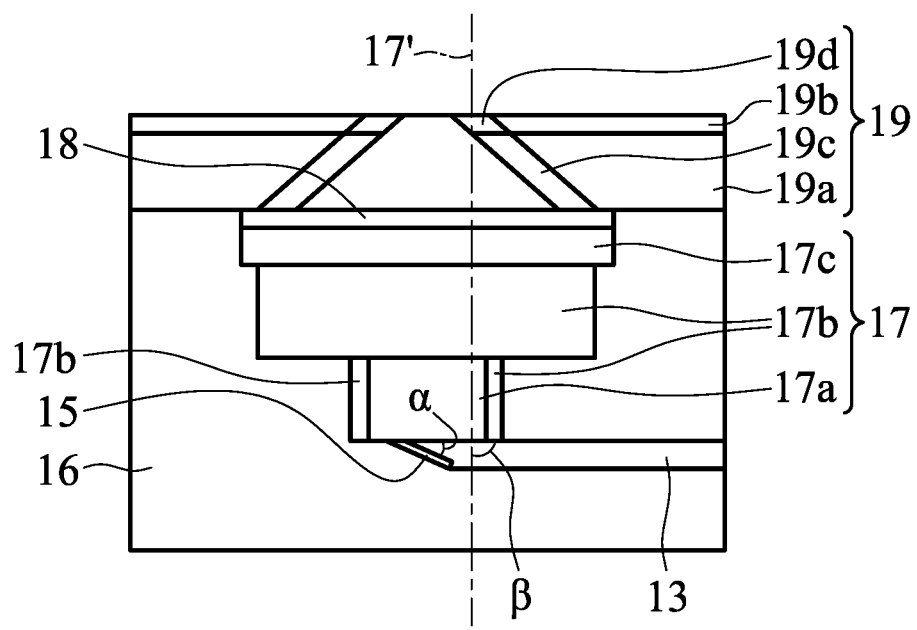

Example 10 was similar to Example 9, and difference in Example 10 was the area of the first layer 17a of the filter 17 being decreased to 16% of its original area, and the area of the second layer 17b being decreased to 81% of the its original area. As such, a filter 17 with a narrow front and wide back structure was obtained, as shown in FIG. 10. In addition, the external peripheral of the first layer 17a (iron disk with a diameter of 15 cm) was surrounded by a material of the second layer 17b with a thickness of 5 cm (composed of 1 part by volume of aluminum fluoride, 0.517 parts by volume of aluminum, and 0.017 parts by volume of lithium fluoride). In this embodiment, the material of the second layer 17b (at the external peripheral of the first layer 17a) and the material of the first layer 17a (iron) have a volume ratio of 9:7. The epithermal neutron flux, the fast neutron dose rate, and the fast neutron dose per epithermal neutron fluence of the neutron beam produced by the neutron beam source generator are tabulated in Table 5.

Example 11

Figure 11:
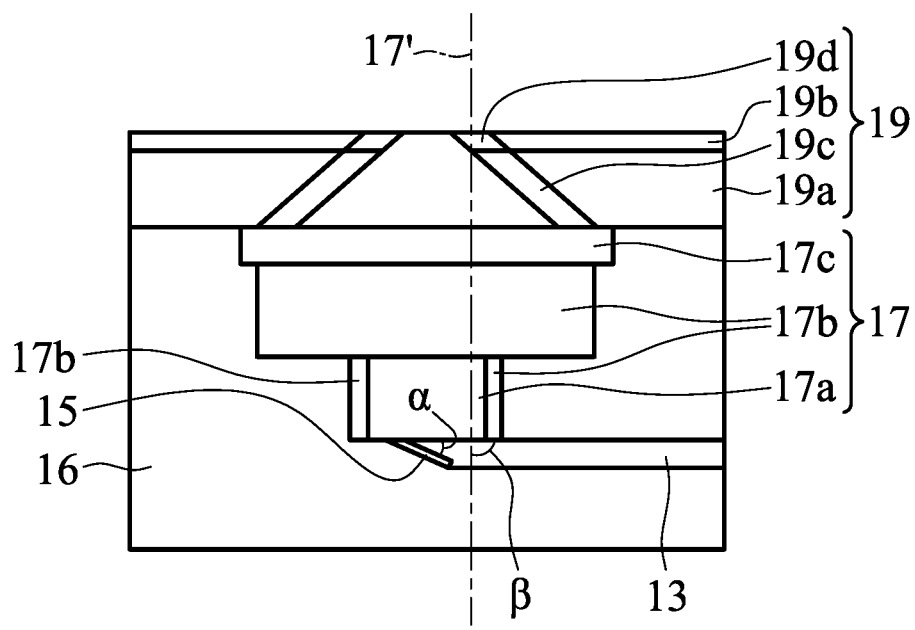

Example 11 was similar to Example 10 except that the bismuth layer 18 between the collimator element 19 and the filter 17 was omitted in Example 11, as shown in FIG. 11. The epithermal neutron flux, the fast neutron dose rate, and the fast neutron dose per epithermal neutron fluence of the neutron beam produced by the neutron beam source generator are tabulated in Table 5.

Example 12

Figure 12:
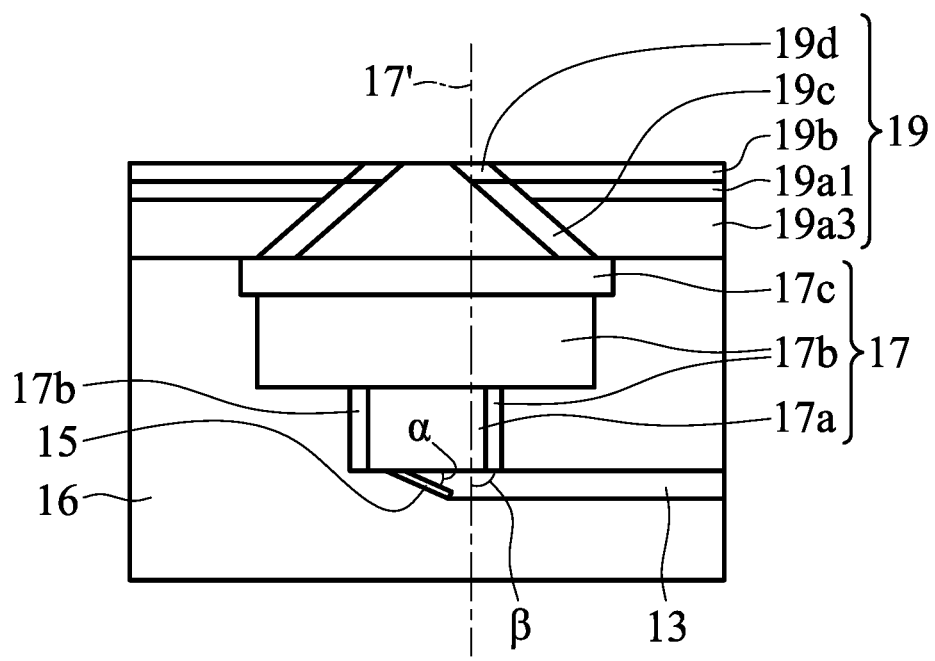

Example 12 was similar to Example 11 except that the shielding material 19a was replaced with 2 layers, a 5 cm-thick layer of polyethylene mixed with 40 wt % of lithium carbonate (19a1) and a 15 cm-thick lead layer (19a3), as shown in FIG. 12. The epithermal neutron flux, the fast neutron dose rate, and the fast neutron dose per epithermal neutron fluence of the neutron beam produced by the neutron beam source generator are tabulated in Table 5.

Example 13

Figure 13:
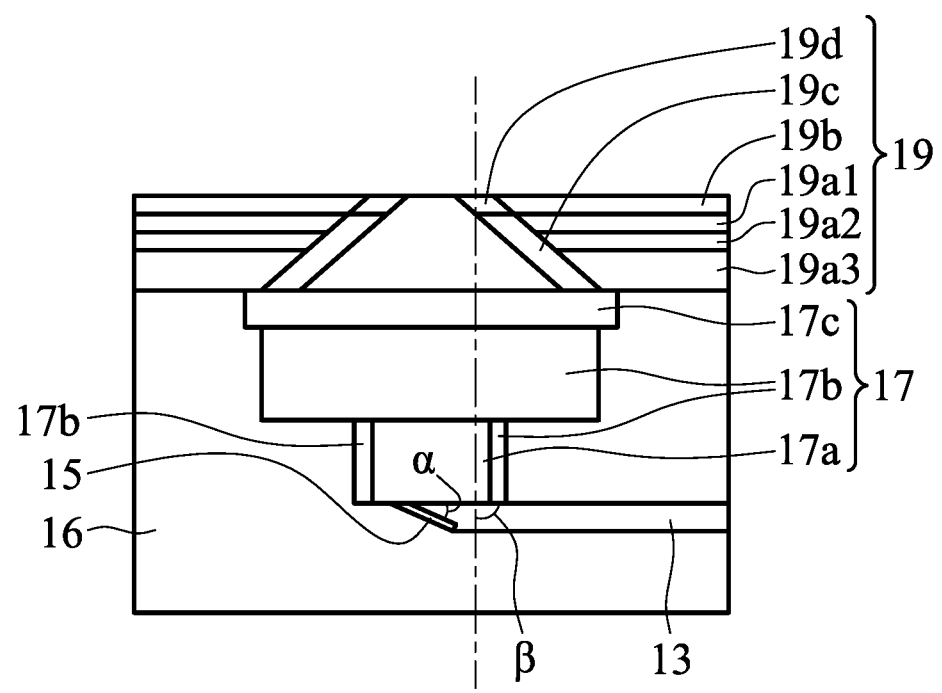

Example 13 was similar to Example 12 except that the thickness of the polyethylene mixed with 40 wt % of lithium carbonate layer 19a1 in the shielding material 19a was reduced to 1 cm, and a 4 cm-thick Teflon layer 19a2 was added, as shown in FIG. 13. The epithermal neutron flux, the fast neutron dose rate, and the fast neutron dose per epithermal neutron fluence of the neutron beam produced by the neutron beam source generator are tabulated in Table 5.

TABLE 5

|  | Example 9 (FIG. 9) | Example 10 (FIG. 10) | Example 11 (FIG. 11) | Example 12 (FIG. 12) | Example 13 (FIG. 13) |
|---|---|---|---|---|---|
| Filter | Column-shaped | Narrow front and wide back | Narrow front and wide back, omitting the bismuth layer | Narrow front and wide back, omitting the bismuth layer | Narrow front and wide back, omitting the bismuth layer |
| Shielding material of the collimator element | Polyethylene mixed with 40 wt % of lithium carbonate | Polyethylene mixed with 40 wt % of lithium carbonate | Polyethylene mixed with 40 wt % of lithium carbonate | Polyethylene mixed with 40 wt % of lithium carbonate/Lead | Polyethylene mixed with 40 wt % of lithium carbonate/Teflon/Lead |
| Filter thickness (cm) | 57 | 57 | 57 | 57 | 57 |
| Epithermal neutron flux ($n \cdot cm^{-2} \cdot s^{-1}$) (1 standard deviation) | $4.40 \times 10^9$ (0.11%) | $5.16 \times 10^9$ (0.09%) | $6.51 \times 10^9$ (0.09%) | $7.63 \times 10^9$ (0.08%) | $8.09 \times 10^9$ (0.08%) |
| Fast neutron dose per epithermal neutron fluence ($cGy \cdot cm^2/n$) (1 standard deviation) | $2.34 \times 10^{-11}$ (0.75%) | $2.56 \times 10^{-11}$ (0.70%) | $2.90 \times 10^{-11}$ (0.58%) | $2.73 \times 10^{-11}$ (0.55%) | $2.66 \times 10^{-11}$ (0.54%) |
| Fast neutron dose rate ($cGy \cdot s^{-1}$) (1 standard deviation) | 0.103 (0.74%) | 0.132 (0.69%) | 0.189 (0.57%) | 0.209 (0.54%) | 0.215 (0.53%) |

As shown in Table 5, changing the shape of the filter to a narrow front and wide back structure, omitting the bismuth layer 18, adjusting the thickness of the shielding material 19a (e.g. polyethylene mixed with 40 wt % of lithium carbonate) of the collimator element, or changing the shielding material of the collimator element from the single layered structure to the multi-layered structure (e.g. bi-layered structure of polyethylene mixed with 40 wt % of lithium carbonated/lead, or tri-layered structure of polyethylene mixed with 40 wt % of lithium carbonated/Teflon/lead) could further improve the intensity of epithermal neutron flux.

Example 14

Example 14 was similar to Example 13, and difference in Example 14 was the third layer 17c being changed to a mixed layer of aluminum, magnesium fluoride, and lithium fluoride. The mixed layer was prepared by following steps: 91.80 g of aluminum, 204.20 g of magnesium fluoride, and 2.99 g of lithium fluoride were added to a ball-milling can, and then ball-milled with steel balls until a uniform powder mixture was obtained. The powder mixture was thermal pressed under vacuum ($10^{-2}$ torr) at temperature of 600° C. by pressing pressure of 330 MPa for 30 minutes, thereby obtaining a bulk from the powder mixture. The bulk is a mixed layer composed of 1 part by volume of magnesium fluoride, 0.526 parts by volume of aluminum, and 0.018 parts by volume of lithium fluoride. The epithermal neutron flux, the fast neutron dose rate, and the fast neutron dose per epithermal neutron fluence of the neutron beam produced by the neutron beam source generator are tabulated in Table 6.

Example 15

Example 15 was similar to Example 14, and difference in Example 15 was the proton beams produced by the accelerator had energy of 24 MeV and current of 500 μA (24 MeV/500 μA). The epithermal neutron flux, the fast neutron dose rate, and the fast neutron dose per epithermal neutron fluence of the neutron beam produced by the neutron beam source generator are tabulated in Table 6.

Example 16

Example 16 was similar to Example 14, and difference in Example 16 was the proton beams produced by the accelerator had energy of 19 MeV and current of 300 μA (19 MeV/300 μA). The epithermal neutron flux, the fast neutron dose rate, and the fast neutron dose per epithermal neutron fluence of the neutron beam produced by the neutron beam source generator are tabulated in Table 6.

TABLE 6

|  | Example 13 | Example 14 | Example 15 | Example 16 |
|---|---|---|---|---|
| Third layer of filter | 99 parts by weight of $MgF_2$ and 1 part by weight of LiF | Mixed layer of aluminum, magnesium fluoride, and lithium fluoride | Mixed layer of aluminum, magnesium fluoride, and lithium fluoride | Mixed layer of aluminum, magnesium fluoride, and lithium fluoride |
| Energy and current of proton beam | 30 MeV/1 mA | 30 MeV/1 mA | 24 MeV/500 μA | 19 MeV/300 μA |

TABLE 6-continued

| | Example 13 | Example 14 | Example 15 | Example 16 |
|---|---|---|---|---|
| Filter thickness (cm) | 57 | 57 | 57 | 57 |
| Epithermal neutron flux (n · cm$^{-2}$ · s$^{-1}$) (1 standard deviation) | 8.09 × 10$^9$ (0.08%) | 9.00 × 10$^9$ (0.07%) | 2.99 × 10$^9$ (0.08%) | 1.11 × 10$^9$ (0.24%) |
| Fast neutron dose per epithermal neutron fluence (cGy · cm$^2$/n) (1 standard deviation) | 2.66 × 10$^{-11}$ (0.54%) | 3.37 × 10$^{-11}$ (0.44%) | 3.12 × 10$^{-11}$ (0.44%) | 3.00 × 10$^{-11}$ (0.44%) |
| Fast neutron dose rate (cGy · s$^{-1}$) (1 standard deviation) | 0.215 (0.53%) | 0.303 (0.43%) | 0.093 (0.43%) | 0.033 (0.43%) |

As shown in Table 6, the mixed layer of aluminum, magnesium fluoride, and lithium fluoride serving as the third layer could further enhance the epithermal neutron flux, such that the filter could integrate with the accelerator for producing protons with the lower energy and the lower current to decrease the cost.

Example 17

Example 17 was similar to Example 14, and difference in Example 17 was the mixing ratio of the mixed layer (the third layer) being different, in which 54 g of aluminum, 251.8 g of magnesium fluoride, and 0.8 g of lithium fluoride were weighed and processed to obtain a mixed layer composed of 1 part by volume of magnesium fluoride, 0.251 parts by volume of aluminum, and 0.004 parts by volume of lithium fluoride. The epithermal neutron flux, the fast neutron dose rate, the fast neutron dose per epithermal neutron fluence, and the relative ratio of thermal neutron flux to epithermal neutron flux of the neutron beam produced by the neutron beam source generator are tabulated in Table 7.

Example 18

Example 18 was similar to Example 14, and difference in Example 18 was the mixing ratio of the mixed layer (the third layer) being different, in which 108 g of aluminum, 188.9 g of magnesium fluoride, and 1.6 g of lithium fluoride were weighed and processed to obtain a mixed layer composed of 1 part by volume of magnesium fluoride, 0.667 parts by volume of aluminum, and 0.01 parts by volume of lithium fluoride. The epithermal neutron flux, the fast neutron dose rate, the fast neutron dose per epithermal neutron fluence, and the relative ratio of thermal neutron flux to epithermal neutron flux of the neutron beam produced by the neutron beam source generator are tabulated in Table 7.

TABLE 7

| | Example 14 | Example 17 | Example 18 |
|---|---|---|---|
| Magnesium fluoride (part by volume) | 1 | 1 | 1 |
| Aluminum (parts by volume) | 0.526 | 0.251 | 0.667 |
| Lithium fluoride (Parts by volume) | 0.018 | 0.004 | 0.01 |
| Epithermal neutron flux (n · cm$^{-2}$ · s$^{-1}$) (1 standard deviation) | 9.00 × 10$^9$ (0.07%) | 8.92 × 10$^9$ (0.07%) | 9.34 × 10$^9$ (0.07%) |
| Fast neutron dose per epithermal neutron fluence (cGy · cm$^2$/n) (1 standard deviation) | 3.37 × 10$^{-11}$ (0.44%) | 2.92 × 10$^{-11}$ (0.48%) | 3.48 × 10$^{-11}$ (0.42%) |
| Fast neutron dose rate (cGy · s$^{-1}$) (1 standard deviation) | 0.303 (0.43%) | 0.261 (0.47%) | 0.325 (0.41%) |
| Ratio of thermal neutron flux to epithermal neutron flux (1 standard deviation) | 2.8% | 5.1% | 3.4% |

As shown in Table 7, the volume ratios of aluminum, magnesium fluoride, and lithium fluoride of the mixture layer (the third layer) could be changed to further adjust the epithermal neutron flux, the fast neutron dose rate, the fast neutron dose per epithermal neutron fluence, and the-ratio of thermal neutron flux to the epithermal neutron flux.

It will be apparent to those skilled in the art that various modifications and variations can be made to the disclosed methods and materials. It is intended that the specification and examples be considered as exemplary only, with the true scope of the disclosure being indicated by the following claims and their equivalents.

What is claimed is:

1. A filter, comprising:
    a first layer, a second layer, and a mixed layer of aluminum, magnesium fluoride, and lithium fluoride,
    wherein
    the first layer is composed of iron,
    the second layer is composed of 1 part by volume of aluminum fluoride, 0.25 to 1 parts by volume of aluminum, and 0.013 to 0.02 parts by volume of lithium fluoride,
    the second layer is disposed between the first layer and the mixed layer,
    a material of the second layer further surrounds sidewalls of the first layer, and
    the mixed layer is composed of 1 part by volume of magnesium fluoride, 0.25 to 1 parts by volume of aluminum, and 0.003 to 0.02 parts by volume of lithium fluoride.

2. The filter as claimed in claim 1, wherein an area of the first layer is smaller than an area of the second layer, and the area of the second layer is smaller than an area of the mixed layer.

3. The filter as claimed in claim 1, being applied in a neutron beam source generator.

* * * * *